United States Patent
Yamanaka

(10) Patent No.: US 11,090,265 B2
(45) Date of Patent: Aug. 17, 2021

(54) AQUEOUS PREPARATION FOR EXTERNAL USE

(71) Applicant: MEDRx Co., Ltd., Kagawa (JP)

(72) Inventor: Katsuhiro Yamanaka, Kagawa (JP)

(73) Assignee: MEDRX CO., LTD., Kagawa (JP)

( * ) Notice: Subject to any disclaimer, the term of this patent is extended or adjusted under 35 U.S.C. 154(b) by 0 days.

(21) Appl. No.: 15/546,798

(22) PCT Filed: Jan. 29, 2016

(86) PCT No.: PCT/JP2016/052838
§ 371 (c)(1),
(2) Date: Jul. 27, 2017

(87) PCT Pub. No.: WO2016/121996
PCT Pub. Date: Aug. 4, 2016

(65) Prior Publication Data
US 2018/0015037 A1    Jan. 18, 2018

(30) Foreign Application Priority Data

Jan. 30, 2015  (JP) .............................. JP2015-016365
May 29, 2015  (JP) ................................. 2015-110902

(51) Int. Cl.
*A61K 9/08*    (2006.01)
*A61K 31/19*   (2006.01)
(Continued)

(52) U.S. Cl.
CPC .............. *A61K 9/08* (2013.01); *A61K 9/0014* (2013.01); *A61K 31/19* (2013.01); *A61K 31/196* (2013.01);
(Continued)

(58) Field of Classification Search
None
See application file for complete search history.

(56) References Cited

U.S. PATENT DOCUMENTS 5,256,691 A    10/1993 Suzuki
5,422,102 A    6/1995  Ikeda et al.
(Continued)

FOREIGN PATENT DOCUMENTS

EP    0 209 975 A1    1/1987
EP    0879597 A1     11/1998
(Continued)

OTHER PUBLICATIONS

International Search Report issued in corresponding International Patent Application No. PCT/JP2016/052838 dated Mar. 29, 2016.
(Continued)

*Primary Examiner* — Dominic Lazaro
(74) *Attorney, Agent, or Firm* — Morgan, Lewis & Bockius LLP

(57) ABSTRACT

The purpose of the present invention is to provide an aqueous preparation for external use, said aqueous preparation comprising an acidic drug such as an arylacetic acid nonsteroidal anti-inflammatory analgesic, having an excellent percutaneous absorbability and giving a good feeling in use. The aqueous preparation for external use comprises the acidic drug or a salt thereof, isostearic acid and an alkanol amine. It is preferred that the aqueous preparation according to the present invention for external use further comprises a $C_{2-6}$ aliphatic hydroxy acid and has a pH value of 4.5-7.8. The $C_{2-6}$ aliphatic hydroxy acid is one member or a combination of the same selected from the group consisting of lactic acid, glycolic acid, malic acid, tartaric acid and citric acid.

20 Claims, 1 Drawing Sheet

(51) Int. Cl.
*A61K 31/205* (2006.01)
*A61K 47/10* (2017.01)
*A61K 47/12* (2006.01)
*A61K 47/18* (2017.01)
*A61K 31/196* (2006.01)
*A61K 9/00* (2006.01)

(52) U.S. Cl.
CPC ............ *A61K 31/205* (2013.01); *A61K 47/10* (2013.01); *A61K 47/12* (2013.01); *A61K 47/18* (2013.01)

(56) References Cited

U.S. PATENT DOCUMENTS

| | | | | |
|---|---|---|---|---|
| 6,455,067 | B1* | 9/2002 | Woo ..................... | A61K 9/7053 424/449 |
| 2006/0036220 | A1 | 2/2006 | Kawahara et al. | |
| 2007/0213406 | A1 | 9/2007 | Kawamura et al. | |
| 2010/0099766 | A1* | 4/2010 | Zhang ................ | A61K 9/0014 514/567 |
| 2010/0256174 | A1* | 10/2010 | Yamaguchi ............ | A61P 23/02 514/282 |
| 2011/0319399 | A1* | 12/2011 | Miura .................. | A61K 9/7053 514/226.5 |

FOREIGN PATENT DOCUMENTS

| | | |
|---|---|---|
| JP | H10-182450 A | 7/1998 |
| JP | 2014-101338 A | 6/2014 |
| JP | 2014-172857 A | 9/2014 |
| JP | 2014-208623 A | 11/2014 |
| WO | 2007/070643 A2 | 6/2007 |
| WO | 2007/070695 A2 | 6/2007 |
| WO | 2007/100376 A2 | 9/2007 |

OTHER PUBLICATIONS

Office Action issued in corresponding European Patent Application No. 16743599.9 dated Nov. 12, 2020.
"6. Solubility" Avdeef, Alex Absorption and Drug Development: Solubility, Permeability, and Charge State, 289-291 (2012).

* cited by examiner

[Figure 1]
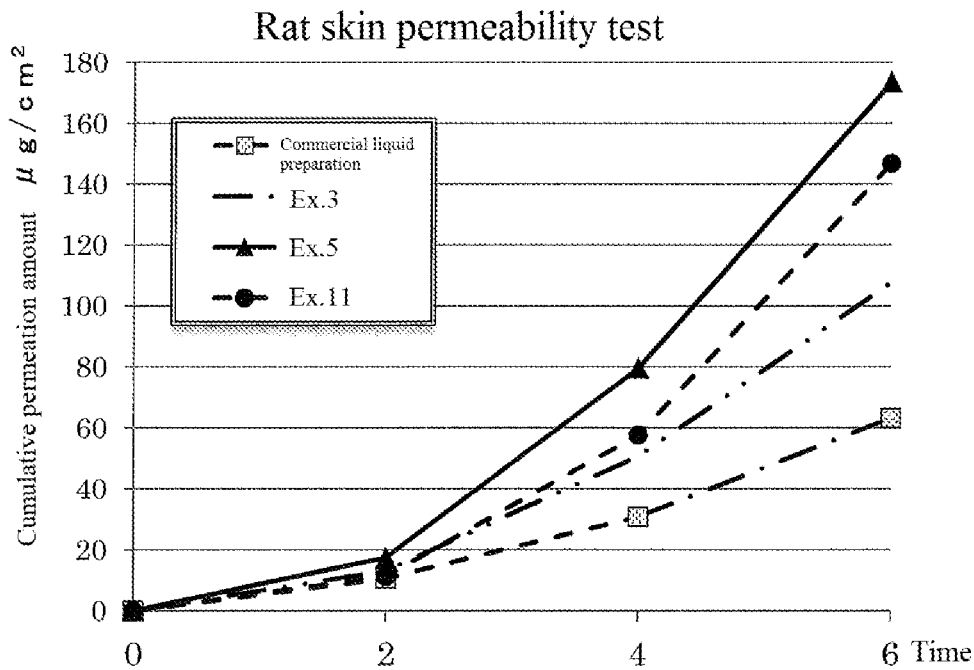
[Figure 2]
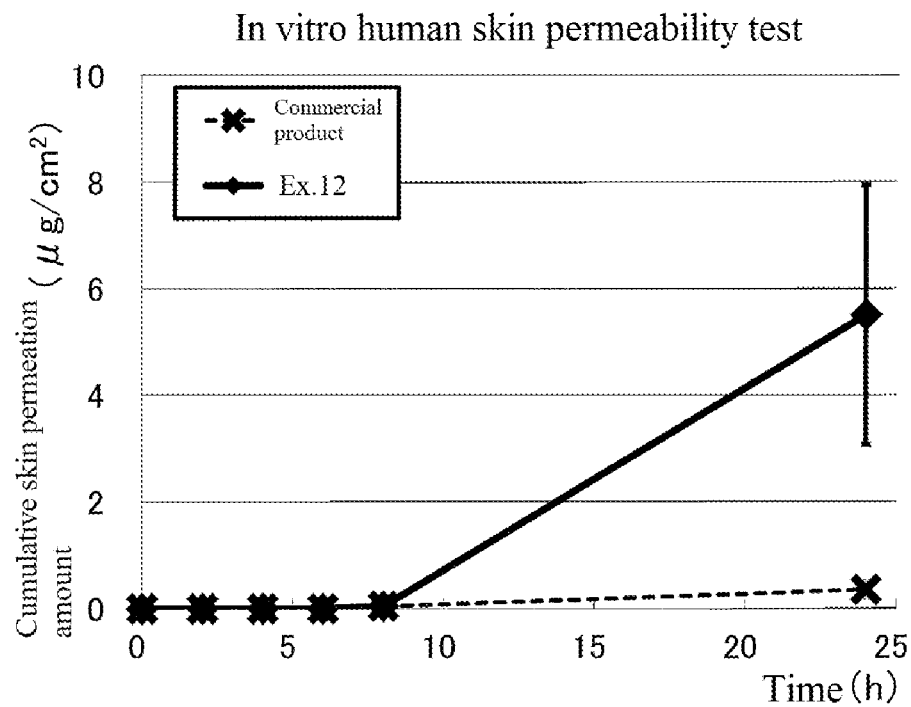

AQUEOUS PREPARATION FOR EXTERNAL USE

TECHNICAL FIELD

The present invention relates to an aqueous preparation for external use comprising an acidic drug or a salt thereof as an active ingredient.

BACKGROUND ART

As the external preparation of the acidic drug, anti-inflammatory analgetic preparations for external use such as phenylacetic acid nonsteroidal anti-inflammatory analgetics like Diclofenac, and propionic acid nonsteroidal anti-inflammatory analgetics like Loxoprofen are broadly known, and various techniques for improving percutaneous absorbability of drugs have been proposed (e.g. Patent Documents 1 to 6).

PRIOR ART DOCUMENTS

Patent Documents

Patent document 1: JP H07-173058 A
Patent document 2: JP H10-182450 A
Patent document 3: JP 2005-336063 A
Patent document 4: JP 2014-208623 A
Patent document 5: JP 2014-172857 A
Patent document 6: JP 2014-101338 A

SUMMARY OF THE INVENTION

Problems to be Solved by the Invention

An object of the present invention is to provide an aqueous preparation for external use having an excellent percutaneous absorbability of acidic drugs and giving a good feeling in use.

Means for Solving Problems

As a result of intensive studies, the present inventors found that the aforementioned problem could be solved by an aqueous preparation for external use comprising isostearic acid and alkanolamine, and completed the present invention. That is, the present invention provides an aqueous preparation for external use comprising an acidic drug or a salt thereof, isostearic acid and alkanolamine.

Preferably, the aqueous preparation for external use according to the present invention further comprises a $C_{2-6}$ aliphatic hydroxy acid, and has pH 4.5 to 7.8.

The $C_{2-6}$ aliphatic hydroxy acid may be one acid or a combination of two or more acids selected from a group consisting of lactic acid, glycolic acid, malic acid, tartaric acid and citric acid.

The acidic drug is preferably an arylacetic acid nonsteroidal anti-inflammatory analgetic.

Preferably, the aqueous preparation for external use according to the present invention further comprises glycerin.

Effects of the Invention

The aqueous preparation for external use according to the present invention has an excellent percutaneous absorbability, and particularly when the drug is an anti-inflammatory analgetic such as an arylacetic acid nonsteroidal anti-inflammatory analgetic, the preparation is expected to exhibit a sufficient anti-inflammatory analgetic effect in a short time.

The aqueous preparation for external use according to the present invention can also be suitably used as a liquid preparation which gives a good feeling in use and is used by being put into an applicator with a foamed resin or ball attached to its tip.

BRIEF DESCRIPTION OF DRAWINGS

FIG. 1 is a graph showing a result of a rat skin permeability test for the aqueous preparations for external use according to the present invention prepared in Examples 3, 5 and 11, and a commercially available 1% Diclofenac sodium liquid preparation.

FIG. 2 is a graph showing a result of a human skin permeability test for the aqueous preparation for external use according to the present invention prepared in Example 12 and a commercially available 1% Diclofenac sodium gel preparation.

MODE FOR CARRYING OUT THE INVENTION

The aqueous preparation for external use according to the present invention comprises an acidic drug or a salt thereof as an active ingredient. The acidic drug can be exemplified by a phenylacetic acid nonsteroidal anti-inflammatory analgetic such as Alclofenac, Diclofenac and Felbinac; an indoleacetic acid nonsteroidal anti-inflammatory analgetic such as Indomethacin, Etodolac and Acemetacin; a salicylic acid nonsteroidal anti-inflammatory analgetic such as salicylic acid, Aspirin, Ethenzamide and Diflunisal; a propionic acid nonsteroidal anti-inflammatory analgetic such as Ibuprofen, Ketoprofen, Zaltoprofen, Suprofen, Pranoprofen, Flurbiprofen and Loxoprofen; a fenamic acid nonsteroidal anti-inflammatory analgetic such as mefenamic acid; an antibiotic such as Cefazolin, Penicillamine, Imipenem and Cilastatin; a barbituric acid drug such as Thiopental, Pentobarbital, Amobarbital and Phenobarbital; an antiallergenic such as cromoglycic acid; and an HMG-CoA reductase inhibitor such as Pravastatin, Rosuvastatin, Atorvastatin and Simvastatin. Among them, the arylacetic acid nonsteroidal anti-inflammatory analgetics such as the phenylacetic acid nonsteroidal anti-inflammatory analgetic and the indoleacetic acid nonsteroidal anti-inflammatory analgetic are preferable, and the phenylacetic acid nonsteroidal anti-inflammatory analgetic is particularly preferred. The salt of the acidic drug which may be used in the present invention can be exemplified by an alkali metal salt such as sodium and potassium; an alkaline earth metal salt such as calcium and magnesium; an ammonium salt; an alkylamine salt such as dimethylamine, diethylamine and trimethylamine; and a cyclic amine salt such as epolamine (hydroxyethylpyrrolidine salt); and the like.

The content of the acidic drug or the salt thereof is not particularly limited but can be selected from a range of e.g. 0.1 to 20 wt %, preferably 0.1 to 10 wt %, particularly preferably 0.5 to 5 wt %. In a case that the content of the acidic drug or the salt thereof is less than the above range, a sufficient drug efficacy may not be obtained, and thus the case is not preferable. In a case that the content of the acidic drug or the salt thereof is more than the above range, the acidic drug or the salt thereof may not be sufficiently dissolved, or otherwise crystals may precipitate over time, and thus the case is not preferable.

The aqueous preparation for external use according to the present invention comprises water as an essential constituent and is typically represented by a liquid preparation, but can be applied to a gel, a cream, a cataplasm and the like. For example, a solution prepared by dissolving an acidic drug or a salt thereof, an isostearic acid, and an alkanolamine, and a $C_{2-6}$ aliphatic hydroxy acid if necessary in a mixture of water and a lower alcohol is a preferable mode of the present invention.

Although it is known to use a fatty acid as a percutaneous absorption promoter, use of the isostearic acid exponentially improves the percutaneous absorbability of the drug compared to use of other fatty acids, in the aqueous preparation for external use comprising the acidic drug. In particular, when the acidic drug is an arylacetic acid nonsteroidal anti-inflammatory analgetic, the percutaneous absorption promoting effect by addition of the isostearic acid is remarkable. The content of the isostearic acid may be selected from a range of e.g. 0.5 to 20 wt %, preferably 2 to 15 wt %, particularly preferably 3 to 10 wt % of the weight of the aqueous preparation for external use. Furthermore, it can be selected from a range of 0.1 to 8 times by mol, preferably 0.5 to 3 times by mol, more preferably 1.0 to 2.5 times by mol, particularly preferably 1.5 to 2.4 times by mol with respect to the acidic drug or the salt thereof.

As the alkanolamine, any of e.g. primary, secondary or tertiary alkanolamines having about 2 to 12 carbon atoms can be used, but tertiary alkanolamines such as triethanolamine and triisopropanolamine are preferred.

The content of the alkanolamine can be selected from a range of 0.4 to 8.0 times by mol, preferably 0.5 to 4.0 times by mol with respect to the content of the isostearic acid. When the acidic drug is a phenylacetic acid nonsteroidal anti-inflammatory analgetic such as Diclofenac, the content of the alkanolamine may be selected from a range of 0.4 to 1.5 times by mol, particularly preferably 0.6 to 1.2 times by mol with respect to the content of the isostearic acid. When the acidic drug is an indoleacetic acid nonsteroidal anti-inflammatory analgetic such as Indomethacin, the content of the alkanolamine may be selected from a range of 2.5 to 8.0 times by mol, preferably 3.0 to 4.0 times by mol with respect to the content of the isostearic acid.

When the aqueous preparation for external use further comprises the $C_{2-6}$ aliphatic hydroxy acid described below, the content of the alkanolamine can be selected from a range of e.g. 0.2 to 2.5 times by mol, preferably 0.3 to 1.2 times by mol, particularly preferably 0.4 to 0.8 times by mol with respect to the sum of the isostearic acid and the aliphatic hydroxy acid. In a case that the amount of the added alkanolamine is out of the above ranges, the aqueous preparation for external use may not be a uniform solution, or otherwise may be separated over time or by stimulation of shake or the like, and thus the case is not preferable.

When the acidic drug is a phenylacetic acid nonsteroidal anti-inflammatory analgetic such as Diclofenac, it is preferred that the content of the alkanolamine is 0.6 to 1.2 times by mol with respect to the content of the isostearic acid, and 0.3 to 0.5 times by mol with respect to the sum of the isostearic acid and the aliphatic hydroxy acid. When the acidic drug is an indoleacetic acid nonsteroidal anti-inflammatory analgetic such as Indomethacin, it is preferred that the content of the alkanolamine is 3.0 to 4.5 times by mol with respect to the content of the isostearic acid, and 0.6 to 0.9 times by mol with respect to the sum of the isostearic acid and the aliphatic hydroxy acid.

The $C_{2-6}$ aliphatic hydroxy acid can be exemplified by lactic acid, glycolic acid, malic acid, tartaric acid and citric acid. One of or a combination of two or more $C_{2-6}$ aliphatic hydroxy acids can be used. When the property of the aqueous preparation for external use is adjusted to an appropriate range by containing the $C_{2-6}$ aliphatic hydroxy acid, the solubility of the acidic drug can be enhanced to obtain a stable external preparation which does not cause crystal precipitation, separation and the like even after long preservation, and furthermore the percutaneous absorbability of the acidic drug is improved. In relation to the aqueous preparation for external use according to the present invention comprising the isostearic acid and the alkanolamine, when its acidity or alkalinity becomes acidic, it become easy to separate, but it becomes a stable liquid preparation by containing the $C_{2-6}$ aliphatic hydroxy acid. The content of the $C_{2-6}$ aliphatic hydroxy acid can be appropriately adjusted so that the liquidity of the aqueous preparation for external use is within an appropriate range described below without any particular limitation. For example, it may be selected from a range of 1.0 to 10 times by mol, preferably 1.0 to 5.0 times by mol, particularly preferably 1.5 to 3.5 times by mol with respect to the acidic drug.

The $C_{2-6}$ aliphatic hydroxy acid preferably comprises at least a tartaric acid or a lactic acid, and particularly preferably comprises a tartaric acid. The inclusion of the tartaric acid improves not only the stability but also particularly the percutaneous of the aqueous preparation for external use. This may be because the tartaric acid is readily soluble in both an aqueous solvent and a fatty solvent, so that after applying the aqueous preparation for external use to the skin, it can remain in a dissolved state even after aqueous solvents such as water and alcohol evaporate, and thus it is easy to penetrate into the skin. A combination of the tartaric acid and the lactic acid is preferably used as the $C_{2-6}$ aliphatic hydroxy acid. When the tartaric acid and the lactic acid are used in combination, their compounding ratio may be selected from a range of tartaric acid:lactic acid=1:1 to 1:3.

The acidity or alkalinity of the aqueous preparation for external use according to the present invention may be selected from a range of pH 4.5 to 7.8, preferably pH 5.6 to 7.5, more preferably pH 5.0 to 6.8, particularly preferably pH 5.0 to 5.8, most preferably pH 5.2 to 5.5. In a case that pH is out of the above range, the stability of the aqueous preparation for external use may deteriorate e.g. crystals are precipitated over time, and skin stimulation or the like may be caused, and thus the case is not preferable. Although the pH of the aqueous preparation for external use can be adjusted according to the contents of the isostearic acid, the alkanolamine and the hydroxy acid described above, it may be further adjusted by using a pH adjuster such as hydrochloric acid, sodium hydroxide and potassium hydroxide.

A lower alcohol used as a solvent by mixing with water can be exemplified by monovalent or divalent alcohols having 2 to 5 carbon atoms such as ethanol, propanol, isopropanol and propylene glycol. One of or a combination of two or more lower alcohols can be used. The content of the lower alcohol may be selected from a range of e.g. 20 to 70 wt %, preferably 40 to 60 wt % in view of e.g. the solubility, the feeling in use and the like of the diclofenac or the salt thereof. In the present invention, it is preferred that the isopropanol and the propylene glycol are used in combination in a ratio of e.g. 1:3 to 3:1, preferably 1:2 to 2:1, particularly preferably 1:1 to 1:2.

The aqueous preparation for external use according to the present invention comprises at least 10 wt %, preferably 20 wt %, particularly preferably not less than 25 wt % of water.

Preferably, the external preparation according to the present invention further comprises glycerin. The inclusion of glycerin can provide an external preparation having excellent immediate effectiveness in which a skin permeation rate of the acidic drug or the salt thereof is improved and after applied to a skin, the acidic drug or the salt thereof rapidly permeates into the skin. The content of glycerin can be selected from a range of e.g. 0.1 to 10 wt %, preferably 0.2 to 5 wt %, particularly preferably 0.2 to 1.0 wt %. In a case that the content of glycerin is less than the above ranges, the effect of improving the permeation rate is hardly obtained, and also in a case that the content is more than the above ranges, the effect is not enhanced, and far from that, the skin permeability may be inferior, and thus the cases are not preferable.

The aqueous preparation for external use according to the present invention may further comprise a lipophilic component as a solubilizer or a percutaneous absorption promoter for the acidic drug or the salt thereof. The lipophilic component can be blended in a range of less than 20 wt %, preferably less than 15 wt % of the aqueous preparation for external use. The lipophilic component can be exemplified by fatty acid esters such as isopropyl myristate, isopropyl palmitate and diethyl sebacate; an N-methylpyrrolidone; a dimethyl isosorbide; and the like. Among them, the N-methylpyrrolidone or the dimethyl isosorbide is preferable.

The aqueous preparation for external use according to the present invention may comprise additives such as a thickening agent, a moisturizer, a dissolution aid, a stabilizer and a perfume, as necessary. The thickening agent can be exemplified by celluloses such as methylcellulose, hydroxymethylcellulose, hydroxyethylcellulose, carmellose, carmellose sodium and carmellose calcium; polyvinylpyrrolidone; polyvinyl alcohol; carboxyvinyl polymer; a polyacrylate such as sodium polyacrylate; and the like. The content of the thickening agent can be selected from a range of e.g. 0.05 to 20 wt %. When the aqueous preparation for external use according to the present invention is a liquid preparation, it can be selected from a range of 0.05 to 0.5 wt %. The stabilizer can be exemplified by sodium sulfite, sodium pyrosulfite and the like.

EXAMPLES

Hereinafter, the present invention will be described in more detail with reference to Examples, but the present invention is not limited by these Examples at all.

[Production of the Aqueous Preparation for External Use]

Aqueous preparations for external use having the compositions (wt %) shown in Table 1 and Table 2 were produced. The pH of each preparation was measured. Also, the appearance when a glass container was filled with the aqueous preparation for external use was observed with naked eyes. The results are collectively shown in Tables 1 and 2.

The appearance was evaluated according to the following criteria.

○: Clear solution

Δ: A transparent solution was obtained, but it separated into an oil phase and an aqueous phase over time or by stimulation of shake or the like

[Skin Permeability Test]

A skin permeability test using a franz cell was carried out according to a conventional method for the produced aqueous preparation for external use and a commercially available 1% Diclofenac sodium liquid preparation. For the test, skins excised from abdomens of rats (5 weeks old, Wistar rat, male) were used. Sampling was carried out 2, 4, and 6 hours after the start of the test. The cumulative permeation amounts after 6 hours are shown in Tables 1 and 2 altogether. A graph indicating transitions of the cumulative skin permeation amounts of the preparations of Examples 3, 5 and 11 and the commercially available liquid preparation is shown in FIG. 1.

TABLE 1

|  | Ex. 1 D28 | Ex. 2 D20 | Ex. 3 D63 | Ex. 4 D67 | Comp Ex. 1 D31 | Comp Ex. 2 D32 | Comp Ex. 3 D35 | Comp Ex. 4 D36 | Comp Ex. 5 D25 |
|---|---|---|---|---|---|---|---|---|---|
| Diclofenac Na | 10 | 10 | 10 | 10 | 10 | 10 | 10 | 10 | 10 |
| Isostearic acid | 40 | 40 | 40 | 40 | | | | | |
| Decanoic acid | | | | | 40 | 40 | | | |
| Levulinic acid | | | | | | | 40 | 40 | |
| Lactic acid | | | 10 | 10 | | | | | |
| Triisopropanolamine | 40 | | | | 40 | | 40 | | |
| Triethanolamine | | 40 | 40 | 40 | | 40 | | 40 | |
| Glycerin | | | | 10 | | | | | |
| Isopropanol | 200 | 200 | 200 | 200 | 200 | 200 | 200 | 200 | 200 |
| Pure water | 305 | 305 | 300 | 295 | 305 | 305 | 305 | 305 | 345 |
| Propylene glycol | 305 | 305 | 300 | 295 | 305 | 305 | 305 | 305 | 345 |
| Dimethyl isosorbide | 100 | 100 | 100 | 100 | 100 | 100 | 100 | 100 | 100 |
| total | 1000 | 1000 | 1000 | 1000 | 1000 | 1000 | 1000 | 1000 | 1000 |
| pH | 7.5 | 7.8 | 5.5 | 7.8 | 6.7 | 7.1 | 5.8 | 6.0 | 6.2 |
| Appearance | ○ | ○ | Δ | ○ | ○ | ○ | ○ | ○ | ○ |
| Cumulative skin permeation amount (6 hr) | 85.6 | 99.6 | 108 | 145.0 | 9.1 | 5.3 | 10.0 | 4.7 | 19.2 |

The aqueous preparations for external use of Examples 1 and 2 of the present invention comprising the isostearic acid and the alkanolamine showed a higher skin permeability compared to the preparation of Comparative Example 5 which does not comprise both of them. The liquid preparations of Comparative Examples 1 to 4 comprising a decanoic acid and a levulinic acid as fatty acids instead of the isostearic acid had skin permeability inferior to that of the preparation of Comparative Example 5. The preparation of Example 3 showed skin permeability superior to that of the preparation of Example 2 by further containing a lactic acid. The preparation of Example 4 showed skin permeability superior to that of the preparation of Example 3 by further containing glycerin.

TABLE 2

|  | Ex. 5 D70 | Ex. 6 D72 | Ex. 7 D76 | Ex. 8 D80 | Ex. 9 D78 | Ex. 4 D67 | Ex. 10 D73 | Ex. 11 D66 |
|---|---|---|---|---|---|---|---|---|
| Diclofenac Na | 10 | 10 | 10 | 10 | 10 | 10 | 10 | 10 |
| Isostearic acid | 55 | 50 | 55 | 55 | 55 | 40 | 55 | 60 |
| Lactic acid | 10 | 10 | 10 | 10 | 7 | 10 | 10 | 10 |
| Triethanolamine | 40 | 40 | 35 | 30 | 33 | 40 | 40 | 40 |
| Glycerin | 5 | 5 | 5 | 5 | 5 | 10 | 10 | |
| Isopropanol | 200 | 200 | 200 | 200 | 200 | 200 | 195 | 200 |
| Pure water | 295 | 295 | 295 | 295 | 295 | 295 | 295 | 295 |
| Propylene glycol | 295 | 295 | 295 | 305 | 295 | 295 | 295 | 295 |
| Dimethyl isosorbide | 90 | 95 | 92 | 90 | 100 | 100 | 90 | 90 |
| total | 1000 | 1000 | 1000 | 1000 | 1000 | 1000 | 1000 | 1000 |
| pH | 7.3 | 7.3 | 7.3 | — | — | 7.5 | 7.3 | 7.3 |
| Appearance | ○ | ○ | ○ | Δ | ○ | ○ | ○ | ○ |
| Cumulative skin permeation amount (6 hr) | 175.2 | 165.3 | 115.6 | 103.1 | 94.6 | 145.1 | 162.4 | 146.8 |

All of the aqueous preparations for external use of Examples 4 to 11 comprising 4 to 6 wt % of isostearic acid showed good skin permeability. There was a tendency that, among them, the preparations having higher contents of the isostearic acid showed superior skin permeability. There was a tendency that the aqueous preparations for external use of Examples 7 to 9 having low contents of the organic amine showed somewhat inferior skin permeability.

As shown in FIG. 1, the aqueous preparation for external use according to the present invention had excellent skin permeability and showed up to about 3 times the Diclofenac skin permeability of the commercially available Diclofenac sodium liquid preparation. In particular, the liquid preparation of Example 5 comprising glycerin had a high permeation rate.

The appearance was evaluated according to the following criteria.

○: Clear solution

Δ: A transparent solution was obtained, but it separated into an oil phase and an aqueous phase over time or by stimulation of shake or the like A skin permeability test using the franz cell was carried out according to the conventional method for the aqueous preparations for external use of Examples 12 to 15. For the test, skins of swines (Yucatan Micropig, male, 5 months old) were used. Sampling was carried out 8 and 24 hours after the start of the test. The cumulative skin permeation amounts ($\mu g/cm^2$) are shown altogether in Table 3.

TABLE 3

|  | Ex. 12 D94 | Ex. 13 D87 | Ex. 14 D88 | Ex. 15 D91 | Ex. 16 D92 | Ex. 17 D93 | Ex. 18 D95 | Ex. 19 D97 | Ex. 20 D99 | Ex. 21 D106 |
|---|---|---|---|---|---|---|---|---|---|---|
| Diclofenac Na | 10 | 10 | 10 | 10 | 10 | 10 | 10 | 10 | 10 | 10 |
| Isostearic acid | 20 | 55 | 20 | 20 | 15 | 10 | 15 | 15 | 20 | 20 |
| Lactic acid | 5 | 10 | 10 | 10 | 10 | 10 | | 5 | 5 | 5 |
| Tartaric acid | 5 | | | | 5 | 10 | 5 | 5 | 5 | 3 |
| Citric acid | | | | | | | 5 | | | 2 |
| Triethanolamine | 10 | 40 | 10 | 13 | 10 | 10 | 10 | 5 | 10 | 10 |
| Glycerin | 5 | 5 | 5 | 5 | 5 | 5 | 5 | 10 | 10 | 5 |
| Isopropanol | 265 | 200 | 265 | 265 | 265 | 265 | 270 | 270 | 265 | 265 |
| Pure water | 295 | 305 | 295 | 295 | 295 | 295 | 295 | 295 | 290 | 295 |
| Propylene glycol | 295 | 305 | 295 | 292 | 295 | 295 | 295 | 295 | 295 | 295 |
| Dimethyl isosorbide | 90 | 70 | 90 | 90 | 90 | 90 | 90 | 90 | 90 | 90 |
| total | 1000 | 1000 | 1000 | 1000 | 1000 | 1000 | 1000 | 1000 | 1000 | 1000 |
| pH | 5.33 | 7.48 | 5.72 | 6.45 | 4.9 | 4.47 | 5.4 | 4.8 | 4.76 | 5.55 |
| Appearance | ○ | ○ | ○ | ○ | Δ | Δ | ○ | Δ | Δ | ○ |
| Cumulative skin permeation amount (6 hr) | 10 | 0.31 | 5.83 | 1.56 | | | | | | |
| Cumulative skin permeation amount (24 hr) | 68.7 | | 56.2 | 23.6 | | | | | | |

Examples 12 to 21

Aqueous preparations for external use having the compositions (wt %) shown in Table 3 were produced. The pH of each preparation was measured. Also, the appearance when a glass container was filled with the aqueous preparation for external use was observed with naked eyes. The results are shown in Table 3 altogether.

All of the external preparations within a range of pH 5.0 to 7.5 were stable liquid preparations which did not cause separation or the like even after preservation.

A human skin permeability test using the franz cell was carried out according to the conventional method for the prepared aqueous preparation for external use of Example 12 and a commercially available 1% diclofenac sodium gel preparation. A graph indicating transitions of the cumulative skin permeation amounts of the diclofenac is shown in FIG. 2.

Examples 2-1 to 2-6

Aqueous preparations for external use comprising indomethacin as an active ingredient having the compositions (wt %) shown in Table 4 were produced. The pH of each preparation was measured. Also, the appearance when a glass container was filled with the aqueous preparation for external use was observed with naked eyes. The results are shown in Table 4.

The appearance was evaluated according to the following criterion.
○: Clear solution A skin permeability test using the franz cell was carried out according to the conventional method for the aqueous preparations for external use of Examples 2-1 to 2-5 and the commercially available 1% Indomethacin liquid preparation. For the test, skins of swines (Yucatan Micropig, male, 5 months old) were used. The cumulative skin permeation amounts ($\mu g/cm^2$) until 24 hours after the start of the test are shown in Table 4.

TABLE 4

|  | Ex. 2-1 194-2 | Ex. 2-2 194-3 | Ex. 2-3 194-4 | Ex. 2-4 194-5 | Ex. 2-5 194-6 | Commercial product |
|---|---|---|---|---|---|---|
| Indomethacin | 10 | 10 | 10 | 10 | 10 | |
| Isostearic acid | 20 | 20 | 20 | 14 | 13 | |
| Lactic acid | 5 | 5 | 5 | 5 | 5 | |
| Tartaric acid | 5 | 5 | 5 | 5 | 5 | |
| Triethanolamine | 20 | 25 | 30 | 16 | 13 | |
| Glycerin | 5 | 5 | 5 | 5 | 5 | |
| Isopropanol | 265 | 260 | 265 | 265 | 267 | |
| Pure water | 290 | 290 | 285 | 295 | 295 | |
| Propylene glycol | 290 | 290 | 285 | 295 | 297 | |
| Dimethyl isosorbide | 90 | 90 | 90 | 90 | 90 | |
| total | 1000 | 1000 | 1000 | 1000 | 1000 | |
| pH | 6.21 | 6.72 | 7.07 | 5.33 | 5.25 | 5.71 |
| Appearance | ○ | ○ | ○ | ○ | ○ | |
| Cumulative skin permeation amount ($\mu g/cm^2$) | 8.09 | 4.34 | 4.25 | 12.82 | 17.77 | 3.37 |

INDUSTRIAL APPLICABILITY

The aqueous preparation for external use according to the present invention can be utilized as a liquid preparation which rapidly express an excellent anti-inflammatory analgetic effect, particularly as a liquid preparation which is used by being put into an applicator with a foamed resin or ball attached to its tip.

The invention claimed is:

1. An aqueous preparation comprising
   diclofenac or a salt thereof,
   isostearic acid,
   alkanolamine, and
   lactic acid,
   wherein the aqueous preparation does not separate into an oil phase and an aqueous phase, and
   a content of the alkanolamine is in a range of 0.2 to 2.5 times by mol with respect to a sum of the isostearic acid and the lactic acid.

2. The aqueous preparation according to claim 1, wherein the aqueous preparation has pH 4.5 to 7.8.

3. The aqueous preparation according to claim 2, further comprising glycerin.

4. The aqueous preparation according to claim 1, further comprising one or more acids selected from a group consisting of glycolic acid, malic acid, tartaric acid and citric acid.

5. The aqueous preparation according to claim 4, further comprising glycerin.

6. The aqueous preparation according to claim 1, further comprising glycerin.

7. The aqueous preparation according to claim 1, wherein the alkanolamine is tertiary alkanolamine.

8. The aqueous preparation according to claim 7, wherein the tertiary alkanolamine is triethanolamine or triisopropanolamine.

9. The aqueous preparation according to claim 1, further comprising isopropanol.

10. The aqueous preparation according to claim 1, further comprising propylene glycol.

11. The aqueous preparation according to claim 1, further comprising dimethyl isosorbide.

12. The aqueous preparation according to claim 1, wherein the aqueous preparation further comprises isopropanol and a propylene glycol.

13. The aqueous preparation according to claim 1, further comprising isopropanol and propylene glycol in a ratio of 1:3 to 3:1.

14. The aqueous preparation according to claim 1, wherein the aqueous preparation is in a liquid form, a gel form, a cream form or a cataplasm form.

15. The aqueous preparation according to claim 1, wherein the alkanolamine comprises triethanolamine.

16. An aqueous preparation comprising
   diclofenac or a salt thereof,
   isostearic acid,
   alkanolamine, and
   lactic acid,
   wherein the aqueous preparation has pH 4.5 to 7.8,
   the aqueous preparation does not separate into an oil phase and an aqueous phase, and
   a content of the alkanolamine is in a range of 0.2 to 2.5 times by mol with respect to a sum of the isostearic acid and the lactic acid.

17. The aqueous preparation according to claim 16, further comprising isopropanol and propylene glycol in a ratio of 1:3 to 3:1.

18. The aqueous preparation according to claim 16, wherein the aqueous preparation is in a liquid form, a gel form, a cream form or a cataplasm form.

19. The aqueous preparation according to claim 16, wherein the alkanolamine comprises triethanolamine.

20. A method of delivering an acidic drug or a salt thereof to a subject, comprising percutaneously applying the aqueous preparation of claim 1 on a skin of the subject.

* * * * *